(12) United States Patent
Kiyota

(10) Patent No.: US 9,404,074 B2
(45) Date of Patent: Aug. 2, 2016

(54) INCUBATION APPARATUS

(75) Inventor: Yasujiro Kiyota, Shinagawa (JP)

(73) Assignee: NIKON CORPORATION, Tokyo (JP)

( * ) Notice: Subject to any disclaimer, the term of this patent is extended or adjusted under 35 U.S.C. 154(b) by 681 days.

(21) Appl. No.: 11/991,401

(22) PCT Filed: Nov. 10, 2006

(86) PCT No.: PCT/JP2006/322458
§ 371 (c)(1), (2), (4) Date: Mar. 4, 2008

(87) PCT Pub. No.: WO2007/055317
PCT Pub. Date: May 18, 2007

(65) Prior Publication Data
US 2009/0093046 A1    Apr. 9, 2009

(30) Foreign Application Priority Data
Nov. 11, 2005 (JP) .................. 2005-327469

(51) Int. Cl.
| C12M 3/00 | (2006.01) |
| C12M 1/00 | (2006.01) |
| C12M 1/36 | (2006.01) |
| C12M 1/34 | (2006.01) |

(52) U.S. Cl.
CPC ............. *C12M 41/48* (2013.01); *C12M 23/50* (2013.01); *C12M 41/00* (2013.01); *C12M 41/14* (2013.01); *C12M 41/36* (2013.01); *C12M 41/44* (2013.01)

(58) Field of Classification Search
CPC ...... C12M 23/10; C12M 23/12; C12M 41/06; G02B 21/367; G02B 21/24
USPC .................. 435/288.7, 808, 809, 303.1
See application file for complete search history.

(56) References Cited

U.S. PATENT DOCUMENTS

| 5,905,850 A * | 5/1999 | Kaveh .......................... 700/259 |
| 6,673,595 B2 * | 1/2004 | Barbera-Guillem ....... 435/286.2 |
| 2002/0155487 A1 * | 10/2002 | Greenberger et al. ............ 435/6 |

(Continued)

FOREIGN PATENT DOCUMENTS

| JP | A-2001-275659 | 10/2001 |
| JP | A-2004-016194 | 1/2004 |

(Continued)

OTHER PUBLICATIONS

May 31, 2011 Office Action issued in JP Application No. 2005-327469 (with English translation).

(Continued)

*Primary Examiner* — Nathan Bowers
(74) *Attorney, Agent, or Firm* — Oliff PLC

(57) ABSTRACT

An incubation apparatus, including a temperature-controlled room adjusted to be a predetermined environment condition, and incubating a sample of an incubation container inside the temperature-controlled room, includes a carrying apparatus, an imaging section, and an image analyzing section. The carrying apparatus carries the incubation container in the temperature-controlled room. The imaging section photographs a whole of the incubation container inside the temperature-controlled room. The image analyzing section analyzes an operation state of the incubation apparatus or an incubating environment state of the sample based on a total observing image of the incubation container photographed at the imaging section, and outputs an error signal notifying an abnormality of the operation state or the incubating environment state in accordance with the analysis result.

22 Claims, 12 Drawing Sheets

(56) References Cited

U.S. PATENT DOCUMENTS

| | | | |
|---|---|---|---|
| 2003/0054335 A1 | 3/2003 | Taya et al. | |
| 2004/0064013 A1* | 4/2004 | Attias | 600/22 |
| 2004/0101189 A1 | 5/2004 | Green et al. | |
| 2004/0215362 A1 | 10/2004 | Kokubo et al. | |
| 2005/0282268 A1* | 12/2005 | Kagayama | 435/288.7 |
| 2008/0064089 A1* | 3/2008 | Green et al. | 435/305.1 |

FOREIGN PATENT DOCUMENTS

| | | |
|---|---|---|
| JP | U-3104790 | 8/2004 |
| JP | A-2004-321111 | 11/2004 |
| JP | A-2005-034142 | 2/2005 |
| JP | A-2005-192485 | 7/2005 |
| JP | A-2006-055027 | 3/2006 |
| JP | A-2006-141328 | 6/2006 |
| JP | A-2006-238707 | 9/2006 |
| JP | A-2006-271210 | 10/2006 |

OTHER PUBLICATIONS

Jun. 5, 2012 extended European Search Report issued in EP Application No. 06832504.2.

* cited by examiner

INCUBATION APPARATUS

CROSS REFERENCE TO RELATED APPLICATION

This application is a U.S. National Stage application claiming the benefit of prior filed International Application Number PCT/JP2006/322458, filed Nov. 10, 2006, in which the International Application claims a priority date of Nov. 11, 2005 based on prior filed Japanese Application Number 2005-327469, the entire contents of which are incorporated herein by reference.

TECHNICAL FIELD

The present invention relates to an incubation apparatus incubating a sample of an incubation container in a temperature-controlled room which is adjusted to be a predetermined environment condition.

BACKGROUND ART

Conventionally, an incubation apparatus including a temperature-controlled room is generally used to incubate various kinds of microorganisms and cells. In general, for example, a sensor detecting environment conditions such as temperature, humidity, and carbon dioxide concentration, and an environment adjusting apparatus adjusting the above-stated respective parameters are disposed in the temperature-controlled room of the incubation apparatus, and therefore, inside the temperature-controlled room is adjusted to be a predetermined environment condition.

Besides, an incubation apparatus, distinguishing an incubation state of a sample by measuring an area and the number of the cells from a photographed image to perform processes such as an exchange of culture, is disclosed in Patent Document 1.

However, an object of the incubation apparatus in the above-stated Patent Document 1 is just to improve a workability involved in a subculture, and an analysis object thereof is only a state of the sample inside an incubation container. Consequently, there has been a problem in a point that it is impossible to detect an abnormal state caused by a change of an environment state surrounding the incubation container, a trouble of the incubation apparatus, and so on in the above-stated Patent Document 1. For example, a possibility in which the incubation state of the sample may deteriorate in accordance with passage of time when there is a scattering of culture from other incubation containers or a trouble of an incubation apparatus, and so on. Accordingly, a means capable of detecting such abnormal state in early time has been desired.

Patent Document 1: Japanese Unexamined Patent Application Publication No. 2004-16194

DISCLOSURE

Problems to be Solved

The present invention is made to solve the problems of the above-stated conventional art, and an object thereof is to provide an incubation apparatus capable of detecting abnormal states caused by a change of an environment state surrounding an incubation container, a trouble of the incubation apparatus, and so on.

Means for Solving the Problems

A first invention is an incubation apparatus including a temperature-controlled room adjusted to be a predetermined environment condition, and incubating a sample of an incubation container inside the temperature-controlled room, the incubation apparatus includes: a carrying apparatus, an imaging section, and an image analyzing section. The carrying apparatus carries the incubation container in the temperature-controlled room. The imaging section photographs a whole of the incubation container inside the temperature-controlled room. The image analyzing section analyzes one of an operation state of the incubation apparatus and an incubating environment state of the sample based on a total observing image of the incubation container photographed by the imaging section, and outputs an error signal notifying one of an abnormality of the operation state and the incubating environment state in accordance with the analysis result.

In a second invention according to the first invention, the image analyzing section detects an abnormal operation of the carrying apparatus based on a positional displacement of the incubation container extracted from the total observing image, and outputs the error signal when the abnormal operation is detected.

In a third invention according to the first or the second invention, the image analyzing section detects dew condensation inside the incubation container based on a change of a transmitted light amount inside the incubation container, and outputs the error signal when the dew condensation is detected.

In a fourth invention according to any one of the first to the third inventions, the image analyzing section estimates a culture amount inside the incubation container based on luminance and a ratio of respective color components inside the incubation container, and outputs the error signal when an estimated value of the culture amount deviates from a setting range.

In a fifth invention according to any one of the first to the fourth inventions, the image analyzing section detects a scattering of a culture by extracting at least one of the color component outside of the incubation container and a contour from the total observing image, and outputs the error signal when there is the scattering of the culture.

In a sixth invention according to any one of the first to the fifth inventions, the image analyzing section detects an occurrence of mold inside the incubation container based on the transmitted light amount and color information inside the incubation container, and outputs the error signal when the mold occurs.

In a seventh invention according to any one of the first to the sixth inventions, the carrying apparatus carries the incubation container corresponding to the total observing image out of the temperature-controlled room when the error signal is input.

In a eighth invention according to any one of the first to the sixth inventions, further includes: a notifying device performing a warning operation to outside of the incubation apparatus when the error signal is input.

In a ninth invention according to any one of the first to the eighth inventions, further includes: a microscope unit photographing a sample observing image in which a sample inside the incubation container is microscopic observed in every predetermined time when the error signal is not output; and a recording section recording the sample observing image.

Effect

According to an incubation apparatus of the present invention, abnormal states caused by a change of an environment state surrounding an incubation container, a trouble of the incubation apparatus, and so on can be detected.

DETAILED DESCRIPTION OF THE EMBODIMENTS

Configuration of Incubator in Present Embodiment

Hereinafter, an incubator (incubation apparatus) in the present embodiment is described in detail with reference to the drawings.

An incubator 11 has a first casing 12 performing an incubation of a sample and a second casing 13 constituting a controller. The first casing 12 is used under a state disposed on the second casing 13.

Figure 10:
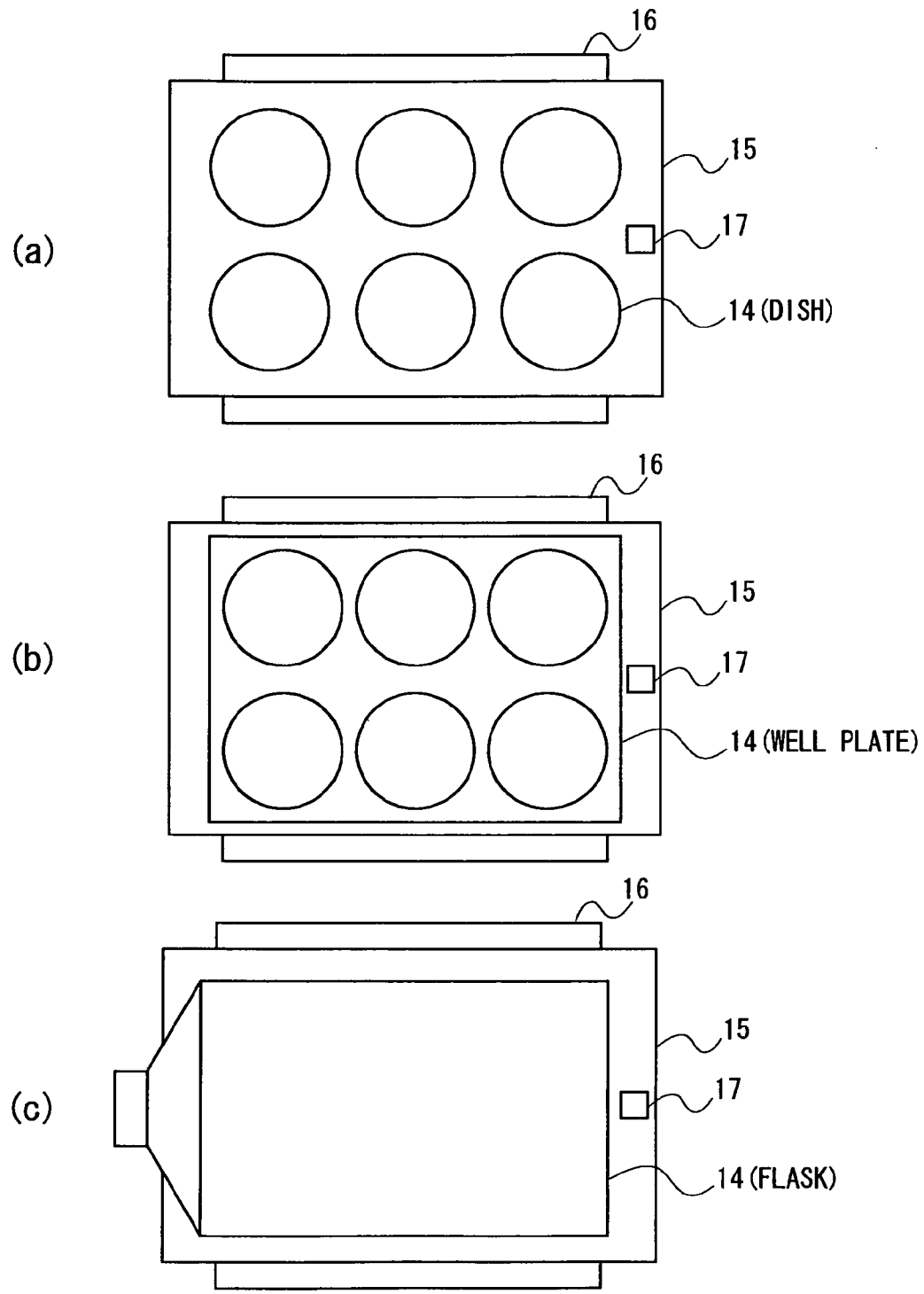
FIG. 10 (A) to FIG. 10 (C) are views showing configurations of incubation containers performing an incubation of a sample.

Here, configurations of incubation containers 14 performing an incubation of a sample are shown in FIG. 10 (A) to FIG. 10 (C). As the incubation container 14 in the present embodiment, a well plate, a flask, a dish, and so on are used. A liquid culture including a pH indicator such as phenol red and a sample (cells and so on) being an object of culture are accommodated in this incubation container 14.

The above-stated incubation container 14 is handled while being mounted on a holder 15 in a transparent tray state. Support pieces 16 are respectively formed outward at both side surfaces of this holder 15. Besides, an identification marker 17 performing an identification of the incubation container is put on the holder 15. As an example of this identification marker 17, for example, a two-dimensional code such as a QR code (a registered trademark), a bar code, and so on can be cited.

Figure 1:
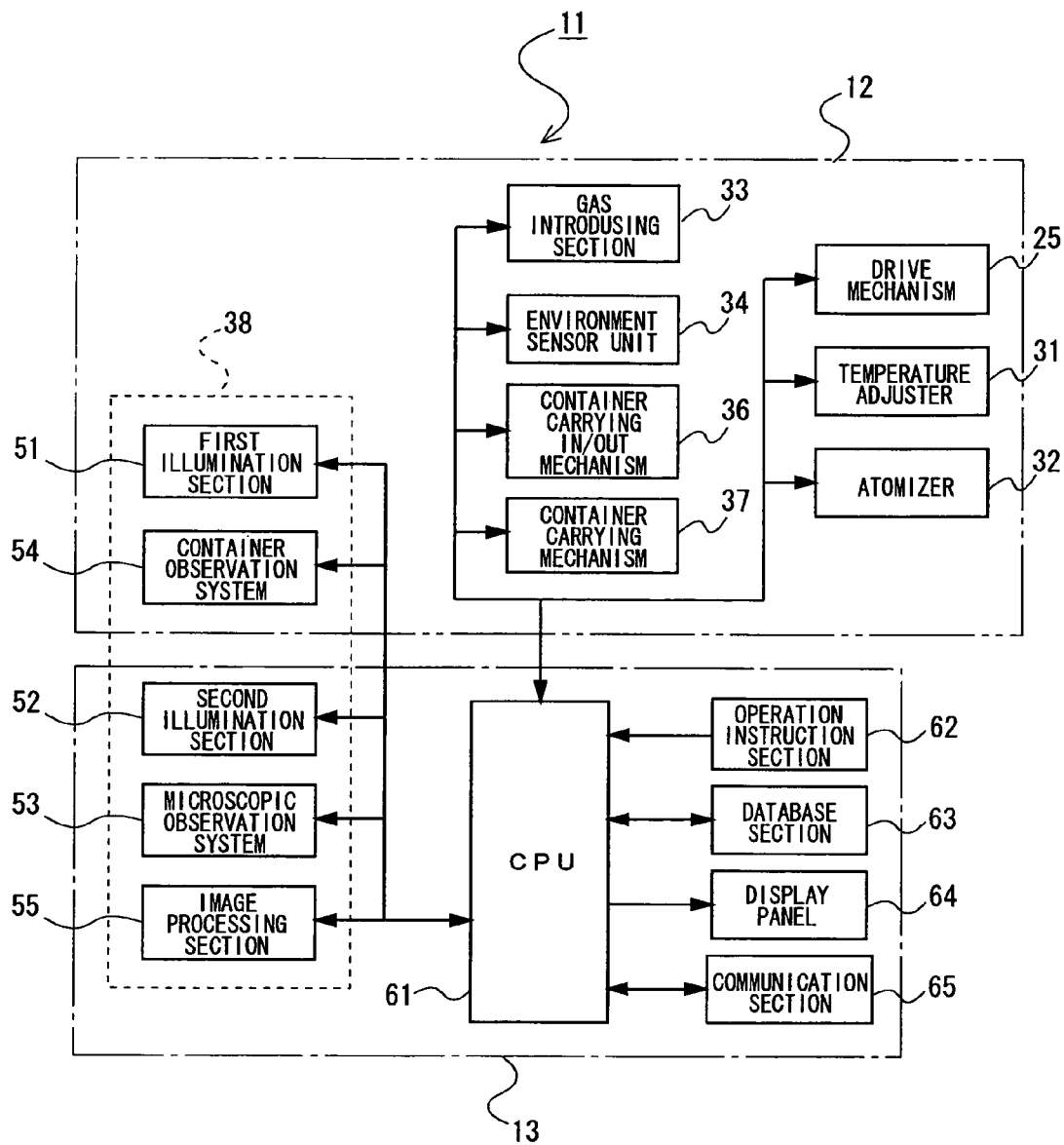
FIG. 1 is a block diagram of an incubator of the present embodiment.
Figure 2:
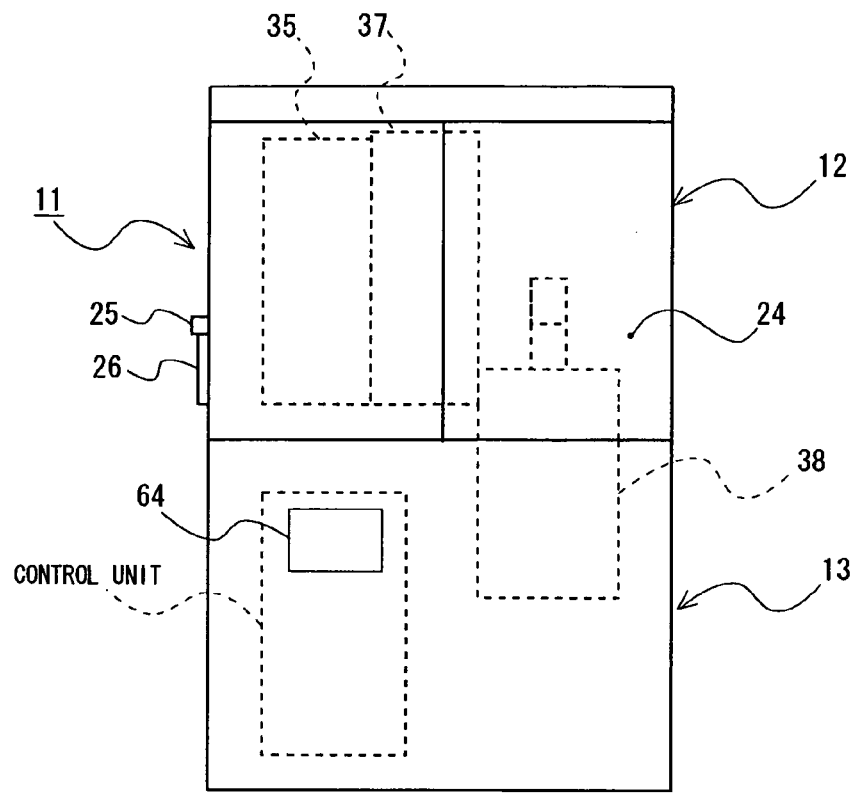
FIG. 2 is a front view of the incubator.
Figure 3:
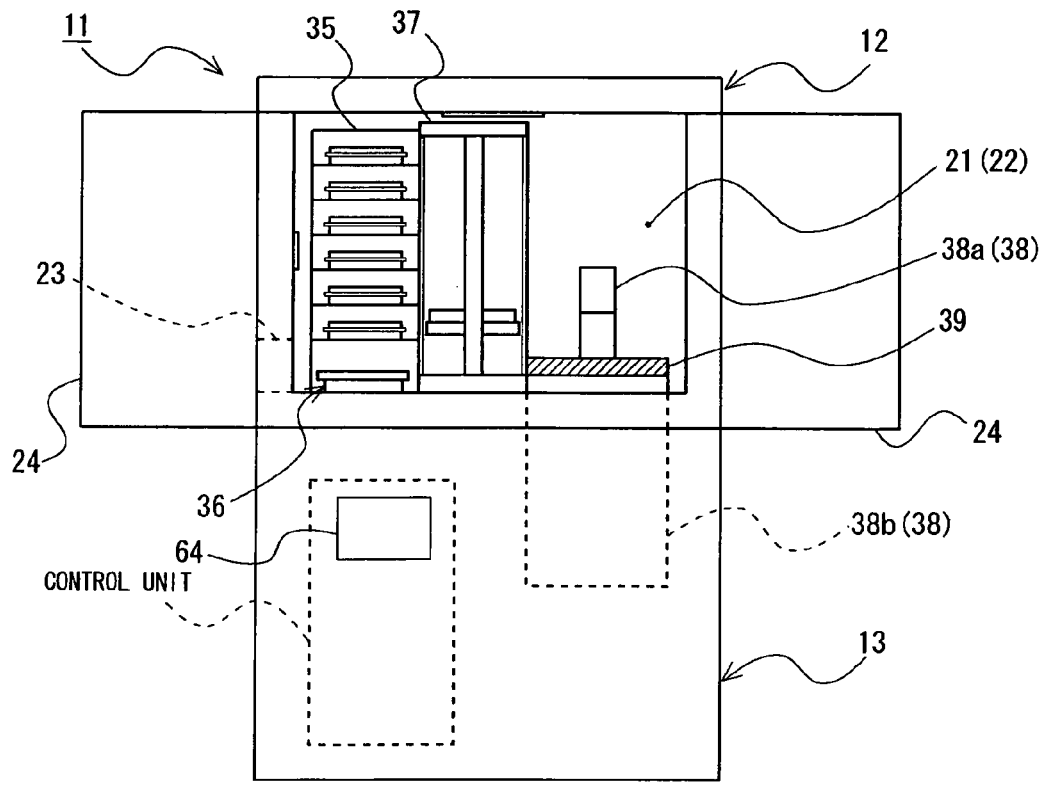
FIG. 3 is a view showing a state in which a front door is opened in FIG. 2.
Figure 4:
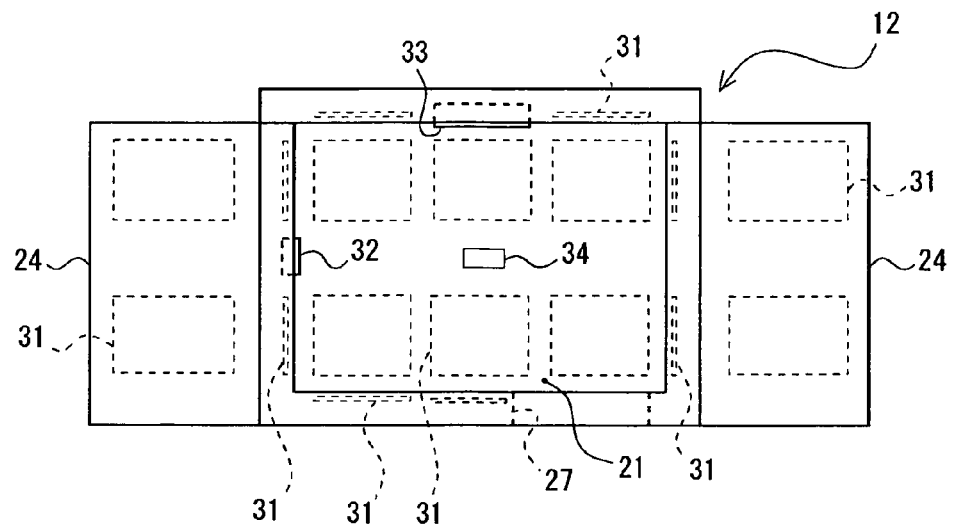
FIG. 4 is a view showing a first casing and a temperature-controlled room.
Figure 5:
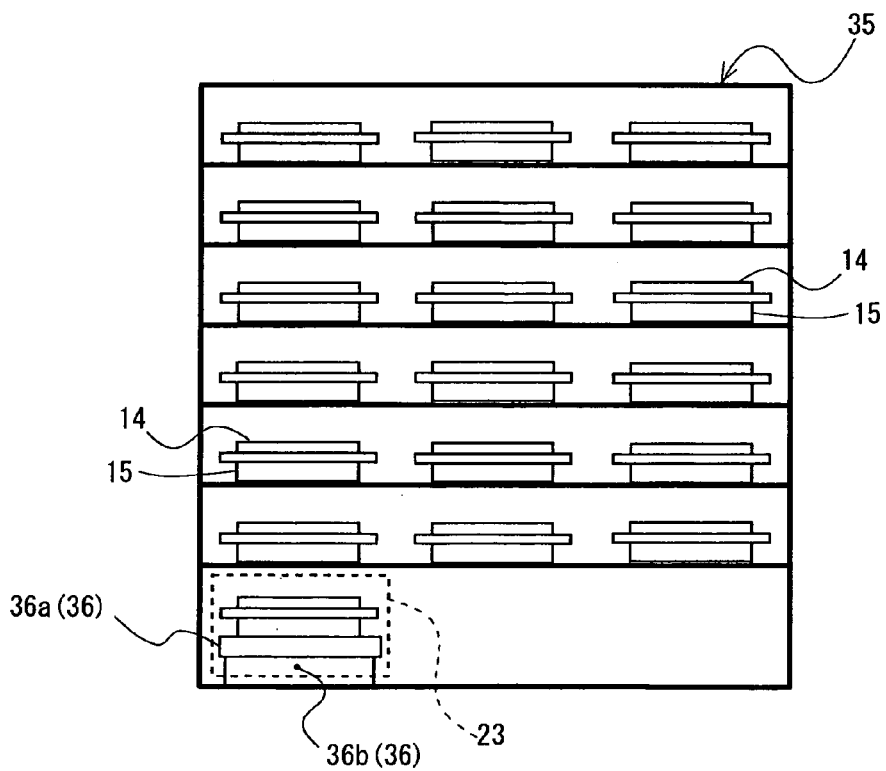
FIG. 5 is a view showing an accommodating state of a stacker viewed from a side direction of the casing.
Figure 6:
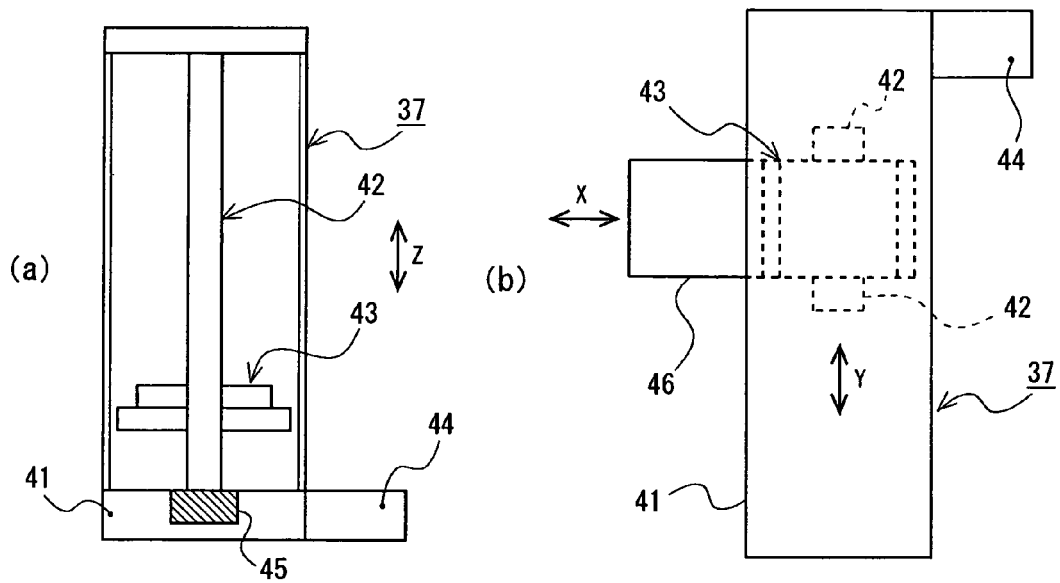
FIG. 6A is a view showing a container carrying mechanism viewed from a front direction of the casing.
FIG. 6B is a view showing the container carrying mechanism viewed from a plane direction of the casing.
Figure 7:
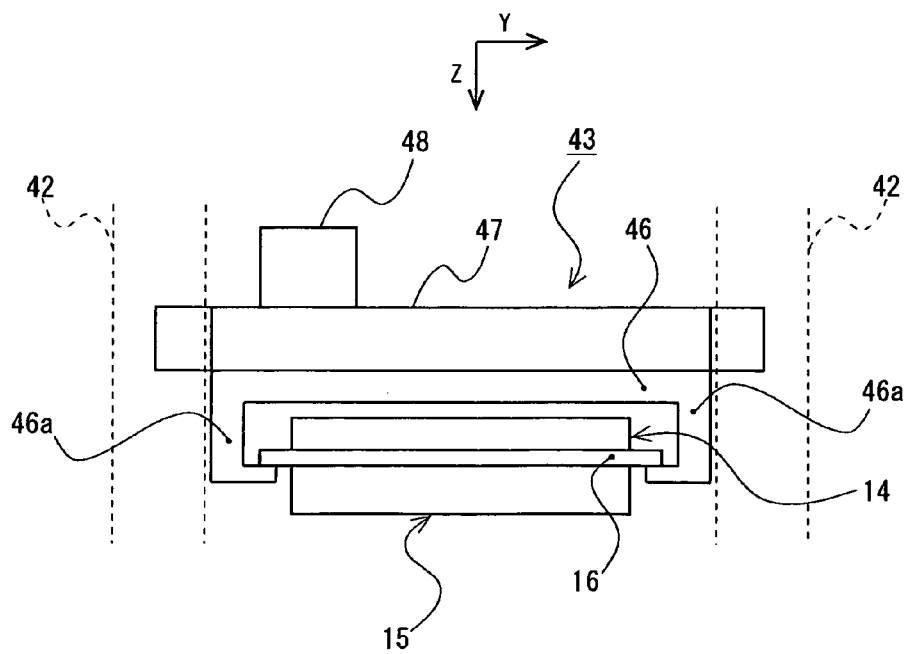
FIG. 7 is a front view showing a configuration of a carrying arm section.
Figure 8:
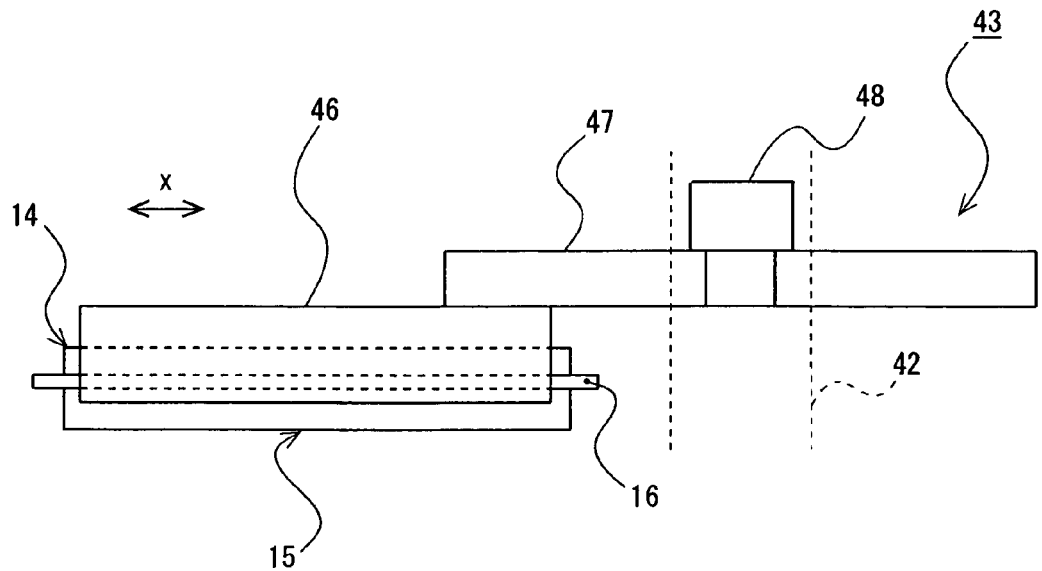
FIG. 8 is a side view showing the configuration of the carrying arm section.

Next, a configuration of the first casing 12 is described based on FIG. 2 to FIG. 4. A temperature-controlled room 21 covered with a heat insulator is formed inside the first casing 12. This temperature-controlled room 21 is connected to the outside via a front opening 22 formed at a front side of the first casing 12 and a carrying in/out port 23 formed at a left side surface of the first casing. The front opening 22 of the first casing is openably/closably locked out by a front door 24 which is a single door or a double door. Incidentally, an example in which the front door 24 is constituted by the double door is shown in FIG. 2 to FIG. 4. Besides, the carrying in/out port 23 is set to be approximately a size in which the incubation container 14 is capable of passing through. This carrying in/out port 23 is openably/closably locked out by an automatic door 26 sliding by a drive mechanism 25. Incidentally, the automatic door 26 may be altered by a door opening/closing manually. Further, an opening 27 is formed at a bottom of the first casing 12 at a right-leaning position viewed from a front side. Incidentally, a later-described observation unit (38) is disposed inside the temperature-controlled room 21 via the opening 27.

A temperature adjuster 31, an atomizer 32, a gas introducing section 33, and an environment sensor unit 34 are accommodated in the temperature-controlled room 21 of the first casing 12. The temperature adjuster 31 includes a Peltier element, and a heating or a cooling by a Peltier effect is performed by inverting an energizing polarity of the Peltier element. Incidentally, the temperature adjuster 31 may be altered by a well-known apparatus, for example, having a constitution such as a combination of a heater unit and a refrigerant circulation system.

Plural temperature adjusters 31 are accommodated at respective wall surfaces of the temperature-controlled room 21, and each of the temperature adjusters 31 can perform a temperature control independently. The atomizer 32 adjusts humidity inside the temperature-controlled room 21 by spraying inside the temperature-controlled room 21. The gas introducing section 33 is connected to a carbon dioxide cylinder (not-shown). This gas introducing section 33 introduces carbon dioxide into the temperature-controlled room 21, to adjust carbon dioxide concentration inside the temperature-controlled room 21. The environment sensor unit 34 detects the temperature, the humidity, and the carbon dioxide concentration inside the temperature-controlled room 21.

Besides, a stocker 35, a container carrying in/out mechanism 36, a container carrying mechanism 37, and an observation unit 38 are accommodated inside the temperature-controlled room 21 of the first casing 12.

The stocker 35 is disposed at left side of the temperature-controlled room 21 viewed from the front side of the first casing 12. The stocker 35 is divided vertically by plural shelves. The incubation container 14 can be accommodated horizontally in the stocker 35. Besides, a lowermost shelf of the stocker 35 corresponds to a position of the carrying in/out port 23 of the first casing 12. A space disposing the container carrying in/out mechanism 36 is formed at the lowermost shelf of the stocker 35.

The container carrying in/out mechanism 36 is provided at the lowermost shelf of the stocker 35. The container carrying in/out mechanism 36 has a carrier table 36a capable of mounting a holder, and a motor unit 36b reciprocating the carrier table 36a toward outside of the carrying in/out port 23.

The container carrying mechanism 37 is disposed at a center of the temperature-controlled room 21 viewed from the front side of the first casing 12. The container carrying mechanism 37 has a rectangular base table 41, a vertical frame 42 extending in a longitudinal direction, and a carrier arm section 43 supporting the holder 15.

The vertical frame 42 is attached to the base table 41 movably in a forward and backward direction (Y direction). A first motor 44 driving the vertical frame 42 in the Y direction is fixed at an outside of the base table 41. Besides, a position in the Y direction of the vertical frame 42 is detected by a position sensor (not-shown) attached to the first motor 44.

The vertical frame 42 is constituted by two guide rails disposed in parallel. The carrier arm section 43 is attached between the vertical frame 42 movably in a longitudinal direction (Z direction). This carrier arm section 43 moves by a rotation of a screw shaft (not-shown) housed in the vertical frame 42. Further, a second motor 45 driving the carrier arm section 43 in the Z direction is attached to the vertical frame 42 at the base table 41 side. Incidentally, a position in the Z direction of the carrier arm section 43 is detected by a position sensor (not-shown) attached to the second motor 45.

The carrier arm section 43 has a container support section 46, a slide mechanism section 47, and a third motor 48. A main body of the container support section 46 is set to be a little wider than a whole width of the holder 15 including the support pieces 16. At both side edges of the container support section 46, a pair of hook claws 46a are disposed to face at a lower side. Tip portions of the respective hook claws 46a face toward inside of the container support section 46, and a mutual interval between the tip portions of the hook claws 46a is set to be slightly larger than the width of the main body portion of the holder 15 excluding the support pieces 16. Accordingly, it is constituted such that the container support section 46 is able to support the holder 15 by an engagement between the support pieces 16 and the hook claws 46a.

The slide mechanism section 47 is disposed at an upper surface side of the container support section 46. This slide mechanism section 47 has a nut section (not-shown) screwing with the above-stated screw shaft. The slide mechanism section 47 slides the container support section 46 in a horizontal direction (X direction) by a drive of the third motor 48. A transfer of the holder 15 mounting the incubation container 14 becomes possible between the stocker 35, the container carrying in/out mechanism 36, or the observation unit 38 and the container carrying mechanism 37 by an operation of the slide mechanism section 47 as stated above. Incidentally, a position in the X direction of the container support section 46 is detected by a position sensor (not-shown) attached to the third motor 48.

The observation unit 38 is disposed at right side of the temperature-controlled room 21 viewed from the front side of the first casing 12. This observation unit 38 is disposed while fit into the opening 27 at the bottom of the first casing 12. This observation unit 38 has a stage 39, an arm 38a throwing out toward upward of the stage 39, and a main body portion 38b. The stage 39 and the arm 38a are disposed inside the temperature-controlled room 21 of the first casing 12, on the other hand, the main body portion 38b is accommodated in the second casing.

Figure 9:
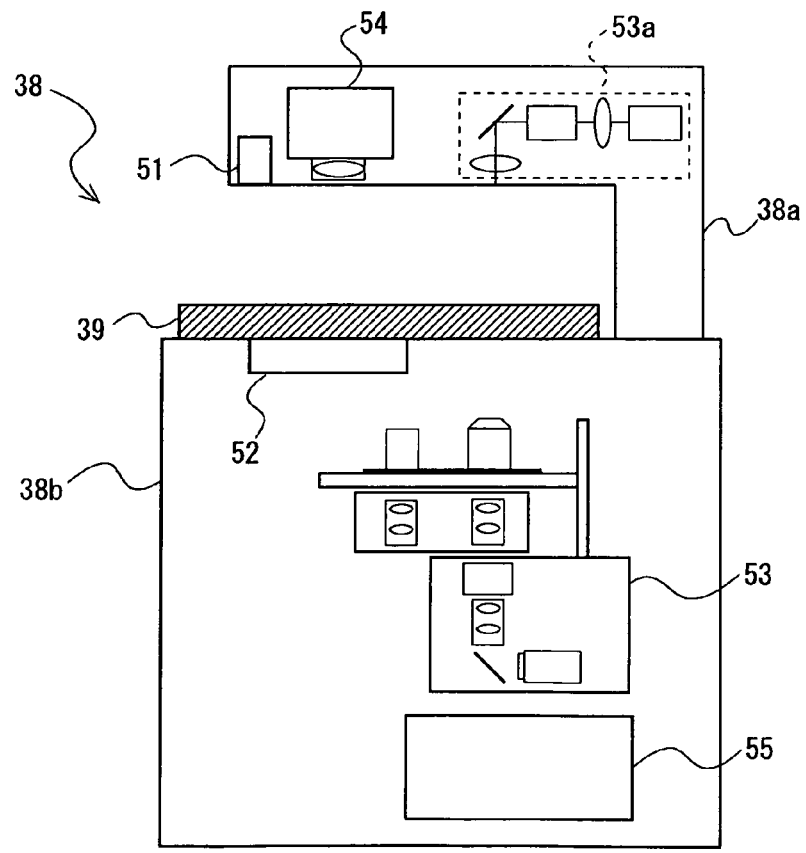
FIG. 9 is a schematic configuration diagram of an observation unit.

FIG. 9 is a schematic diagram showing a configuration of the observation unit 38. The observation unit 38 has the stage 39, a first illumination section 51 and a second illumination section 52, a microscopic observation system 53 having an LED unit 53a, a container observation system 54, and an image processing section 55.

The stage 39 is constituted by a translucent material, and the incubation container 14 is mounted thereon together with the holder 15. Besides, the first illumination section 51 and the LED unit 53a are disposed at the arm 38a, to illuminate the incubation container 14 from an upper side of the stage 39. On the other hand, the second illumination section 52 is housed in the main body portion 38b, to illuminate the incubation container 14 from a lower side of the stage 39.

The microscopic observation system 53 is housed in the main body portion 38b, and it has a microscopic optical system and an image pickup device (both are not shown). This microscopic observation system 53 photographs an image in which a sample is microscopically observed with transmitted light of the incubation container 14 by the illumination of the LED unit 53a (a sample observing image).

The container observation system 54 is accommodated in the arm 38a, and has an imaging optical system and an image pickup device (both are not shown). This container observation system 54 photographs a total observing image of the incubation container 14 by illumination light of the first illumination section 51 or the second illumination section 52.

The image processing section 55 generates a color image data of the sample observing image or the total observing image by performing an A/D conversion of outputs of the microscopic observation system 53 and the container observation system 54, and performing various image processing. Besides, the image processing section 55 performs an image analysis on the image data of the total observing image.

Next, a configuration of the second casing 13 is described. The above-stated main body portion 38b of the observation unit 38 and a control unit are stored in the second casing 13.

The control unit has a CPU 61, an operation instruction section 62, a database section 63, a display panel 64, and a communication section 65.

The CPU 61 is connected to the drive mechanism 25, the temperature adjuster 31, the atomizer 32, the gas introducing section 33, the environment sensor unit 34, the container carrying in/out mechanism 36, the container carrying mechanism 37, the observation unit 38, the operation instruction section 62, the database section 63, the display panel 64, and the communication section 65. The CPU 61 controls the above-stated respective sections in accordance with a predetermined sequence program. Incidentally, the CPU 61 has a clock function for a schedule management.

The operation instruction section 62 has an input device such as a keyboard, and operates each section of the incubator 11 via the CPU 61. Namely, the CPU 61 performs an adjustment of an environment condition inside the temperature-controlled room 21, a carrying in/out of the incubation container 14 into/out of the temperature-controlled room 21, an observation of the sample of the incubation container 14, a carry of the incubation container 14 inside the temperature-controlled room 21, and so on based on an input from the operation instruction section 62. Here, both of an instruction by a direct input of a user and an instruction set by a program in advance are included in the instructions of the operation instruction section 62.

Management data of the incubation container 14, various data required for an image analyzing, and so on are recorded on the database section 63. For example, identification codes of the incubation containers 14, types and shapes of the incubation containers 14, accommodated positions of the incubation containers 14, data of an observation schedule of each incubation container 14 set at the operation instruction section 62, and so on are included in the above-stated management data. Besides, the data of the accommodated positions of the incubation containers 14 may be registered by an input of the user. Otherwise, the CPU 61 may automatically set the accommodated positions of the incubation containers 14 by reading the identification markers 17 of the holders 15 with a camera and so on.

Besides, it is possible to record the image data of the sample observing image and the total observing image in the database section 63. Here, the image data recorded on the database section 63 are recorded while respectively being corresponded to index data containing identification information of the incubation containers 14 and photographed dates and times. Further, a change history of the environment condition (temperature, humidity, carbon dioxide concentration) inside the temperature-controlled room 21 can also be recorded on the database section 63.

Values of the environment condition of the temperature-controlled room 21 output from the CPU 61, and a warning at the time of occurrence of abnormality are displayed on the display panel 64. The communication section 65 controls a data transmission/reception between an external computer (not-shown) and so on, complying with a well-known wireless or wired communication protocol.

(Operations of Incubator in Present Embodiment)

Figure 11:
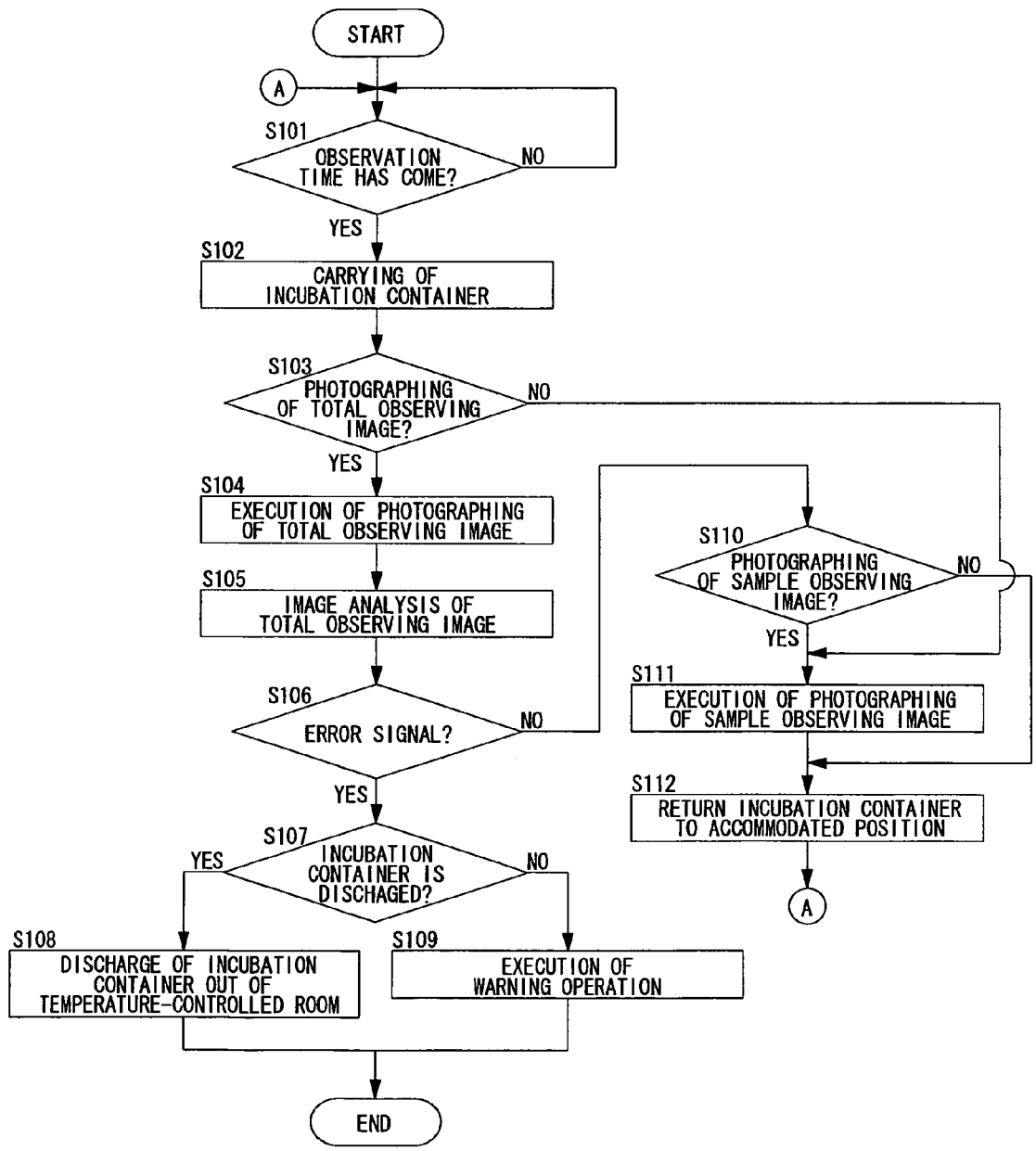
FIG. 11 is a flowchart showing total operations of the incubator in the present embodiment.

Hereinafter, operations of the incubator specific to the present embodiment are described following a flowchart in FIG. 11. The incubator 11 of the present embodiment automatically performs the photographing of the sample observing image and the total observing image based on the observation schedule which is set in advance. The incubator 11 then detects the abnormal states resulting from a change of the environment condition surrounding the incubation container 14, a trouble of the incubation apparatus, and so on based on the total observing image. Incidentally, the actual incubator 11 manages the plural incubation containers 14 simultaneously based on the observation schedule by each incubation container, though the description is made while limiting to a management of one incubation container as a matter of convenience in an example in FIG. 11.

Step 101: The CPU 61 determines whether an observation time of the incubation container 14 has come or not by comparing the observation schedule in the database section 63 and the current date and time. When it is the observation time (YES side), the process goes to S102. On the other hand, when it is not the observation time of the incubation container 14 (NO side), the CPU 61 stands ready for the observation time of the incubation container.

Step 102: The CPU 61 acquires the data of the accommodated position of the incubation container 14 which is an observation object from the database section 63. Next, the CPU 61 instructs the container carrying mechanism 37 to carry the incubation container 14 which is the observation object from the stocker 35 to the observation unit 38. The container carrying mechanism 37 carries out the indicated incubation container 14 from the stocker 35, and mounts the incubation container 14 on the stage 39 of the observation unit 38.

Step 103: The CPU 61 determines whether the photographing of the total observing image is performed or not in the current photographing based on the observation schedule. When the total observing image is photographed (YES side), the process goes to S104. On the other hand, when only the sample observing image is photographed (NO side), the process goes to S111.

Step 104: The CPU 61 instructs the observation unit 38 to photograph the total observing image. The observation unit 38 illuminates the incubation container 14 by lighting at least one of the first illumination section 51 and the second illumination section 52, and photographs the total observing image of the incubation container 14 with the image pickup device of the container observation system 54.

Step 105: The image processing section 55 of the observation unit 38 performs the image analysis for the total observing image. The image processing section 55 outputs an error signal when it is in the abnormal state from a result of the above-stated image analysis, and outputs a normal signal when it does not correspond to the abnormal state. Here, in S105, it is possible to perform the following: (1) Estimation of a culture amount; (2) Detection of a scattering of a culture; (3) Detection of mold inside the incubation container; (4) Detection of a positional displacement of the incubation container; and (5) Detection of dew condensation inside the incubation container. Incidentally, concrete contents of the above-stated (1) to (5) are respectively described later.

Step 106: The CPU 61 determines whether the error signal is input from the image processing section 55 of the observation unit 38 or not. When the error signal is input (YES side), the process goes to S107. On the other hand, when the normal signal is input (NO side), the process goes to S110.

Step 107: The CPU 61 determines whether a setting in which the incubation container 14 is discharged from the temperature-controlled room 21 is made or not when the error signal is input. When the incubation container 14 is discharged (YES side), the process goes to S108. On the other hand, when the incubation container 14 is not discharged (NO side), the process goes to S109.

Here, the setting whether the incubation container 14 is discharged or not can be set individually by a user in advance, by each of the cases of (1) to (5) in S105. For example, when the scattering of the culture or the mold are detected, it is especially desirable to discharge the incubation container 14 which is the observation object from the temperature-controlled room rapidly, because there is an adverse affect on the sample of the other incubation containers 14. On the other hand, when the estimated culture amount is not appropriate or when something is wrong with the container carrying mechanism 37, the temperature adjustor 31, or the like, there is a possibility that it is not an appropriate treatment to discharge the incubation container 14 out of the temperature-controlled room.

Step 108: The CPU 61 instructs the container carrying in/out mechanism 36 and the container carrying mechanism 37 to discharge the incubation container 14 which is the observation object out of the temperature-controlled room. The container carrying mechanism 37 transfers the indicated incubation container 14 from the stage 39 to the container carrying in/out mechanism 36. The CPU 61 opens the automatic door 26 of the carrying in/out port 23, and the container carrying in/out mechanism 36 discharges the incubation container 14 out of the temperature-controlled room 21.

Step 109: The CPU 61 performs warning operations notifying the occurrence of the abnormality. Here, as the warning operations, for example, a warning display on the display panel 64, a transmission of an error notification mail to the external computer by the communication section 65, an audio output by a not-shown buzzer, and so on can be cited. Incidentally, contents of these warning operations can be set by the user in advance by specifying in the operation instruction section 62.

Step 110: The CPU 61 determines whether the photographing of the sample observing image is performed or not in the current photographing based on the observation schedule. When the sample observing image is photographed (YES side), the process goes to S111. On the other hand, when the sample observing image is not photographed (NO side), the process goes to S112.

Step 111: The CPU 61 instructs the observation unit 38 to photograph the sample observing image. The observation unit 38 illuminates the incubation container 14 with the LED unit 53a, and photographs the sample observing image with the image pickup device of the microscopic observation system 53. Incidentally, the image data of the sample observing image is recorded on the database section 63 while being corresponded to the above-stated index data.

Step 112: The CPU 61 instructs the container carrying mechanism 37 to carry the incubation container 14 which is the observation object from the observation unit 38 to the stocker 35. The container carrying mechanism 37 carries out the indicated incubation container 14 from the stage 39, and returns the incubation container 14 to a predetermined position of the stocker 35. After that, the CPU 61 returns to S101 to repeat the above-stated operations.

(Estimation of Culture Amount)

Figure 12:
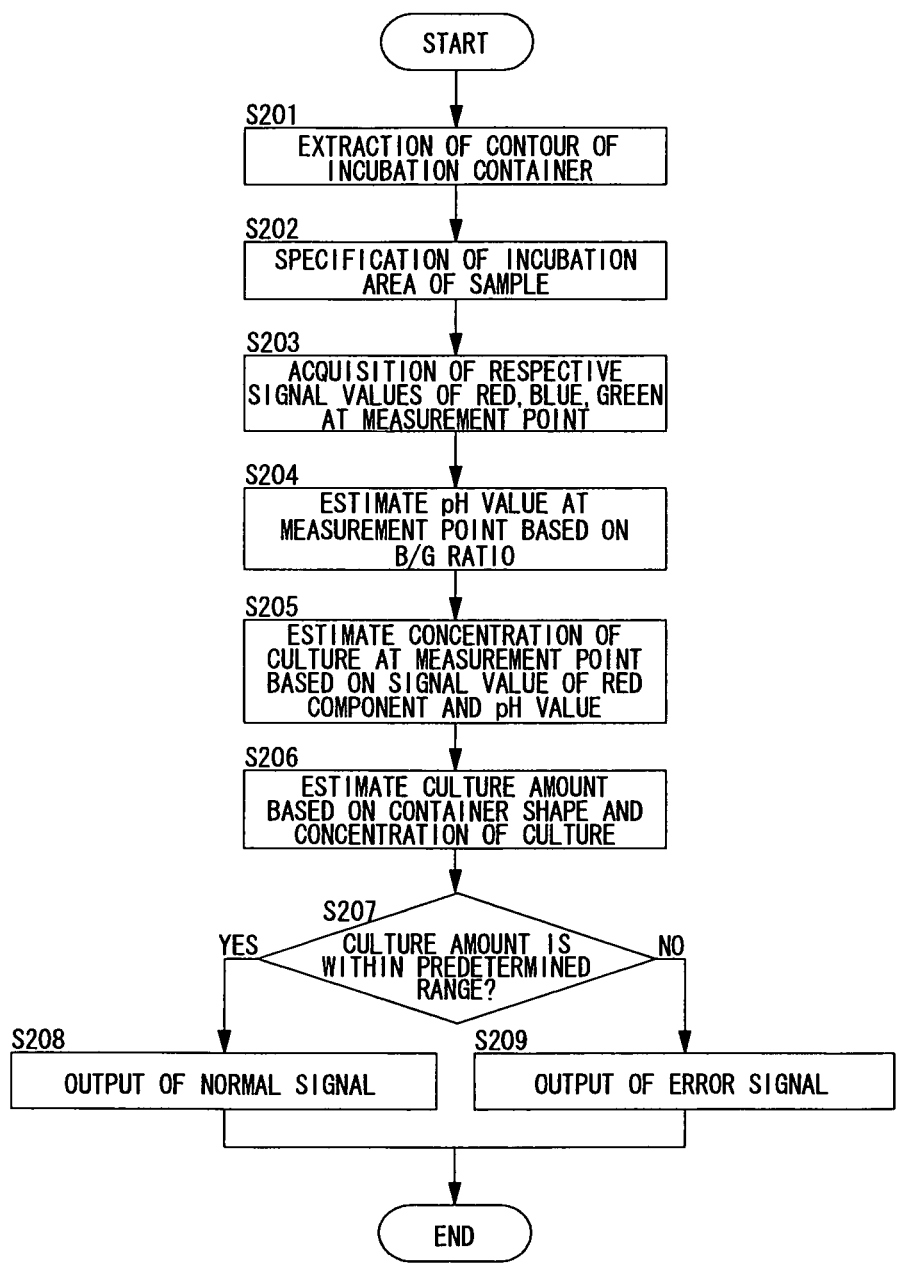
FIG. 12 is a flowchart showing operations in "Estimation of Culture Amount".

Next, the "estimation of the culture amount" in the above-stated S105 is described in detail following a flowchart in FIG. 12. The reason why the "estimation of the culture amount" is performed at S105 is because judgments of a culture exchange or an incubation stop become easier if there is information whether the culture amount is within an appropriate range or not.

Step 201: The image processing section 55 performs an extraction process of edges for the color image data of the total observing image (S104), to extract a contour of the incubation container 14.

Step 202: The image processing section 55 performs a pattern matching between the contour data of the incubation container 14 (S201) and a contour template of the incubation container 14, to specify an area in which an inside of the incubation container 14 is photographed (an incubation area of the sample). When one incubation container has plural individual small containers, the image processing section 55 respectively specifies the incubation areas corresponding to the respective small containers. Incidentally, in this case, the description is made on the assumption that similar operations are performed by each of the individual incubation areas by the following steps.

Step 203: The image processing section 55 determines plural measurement points from among the incubation areas of the sample (S202). Positions of the measurement points in the incubation areas may be determined in advance. The image processing section 55 acquires signal values of three-color components of red, green, blue respectively by each of the measurement points based on the color image data of the total observing image. Incidentally, the signal values of the respective color components become larger as luminance of the color component at the measurement point becomes higher.

Step 204: The image processing section 55 asks a ratio (B/G ratio) between the signal value of the blue component and the signal value of the green component by each measurement point. The image processing section 55 estimates a pH value at each measurement point based on the B/G ratio by, for example, the following expression (1).

$$B/G = 0.56 \times pH^2 - 7.48 \times pH + 25.4 \qquad (1)$$

The above-stated expression (1) is a quadratic function approximately showing a relation of a change between the pH value and the B/G ratio. The "B/G" in the above expression shows the B/G ratio. Besides, the "pH" in the above expression shows the estimated pH value.

Here, the pH value is estimated based on the B/G ratio in the present embodiment because of the following reasons. The present inventors obtained the following knowledge as a result of researches as for the relation between a pH indicator (phenol red) added to the culture and the signal value of each color component of the image.

When a change of color of the phenol red and the ratio of the signal values of the respective color components are compared on the assumption that concentrations of the cultures are the same, the ratio of the blue component increases in accordance with an increase of the pH value, on the other hand, the ratio of the green component decreases. Besides, if the pH value changes, there is not a very large change in the signal value of the red component. Namely, it turns out that a determination of the pH value by the color of the phenol red is synonymous with a determination of the ratio between blue and green. Besides, the color of the phenol red (the ratio between blue and green) non-ambiguously changes in accordance with the pH value. The image processing section 55 estimates the pH value inside the incubation container 14 by the B/G ratio based on the above-stated theory.

Step 205: The image processing section 55 estimates the concentration of the culture at the measurement point based on the signal value of the red component (S203) and the estimated pH value (S204). Concretely speaking, data showing a correspondence between "the signal value of the red component" and "the concentration of the culture", and correction data by the pH value are stored in the database section. The image processing section 55 reads the above-stated respective data from the database section 63, and calculates the concentration of the culture from the signal value of the red component based on the above-stated data.

Here, the concentration of the culture is estimated based on the signal value of the red component because of the following reasons. When the images of the incubation containers 14 having a difference in the concentrations of the cultures are compared on the assumption that the pH values are the same, the color of the culture becomes dark as the concentration of the culture becomes higher. Accordingly, the signal value of the red component becomes large in proportion to the increase of the concentration of the culture. Consequently, it becomes possible to estimate the concentration of the culture by the signal value of the red component. At this time, a change rate between the signal value of the red component and the concentration of the culture is different in accordance with the pH values, and therefore, the image processing section 55 performs the correction by the pH value.

Step 206: The image processing section 55 estimates the culture amount inside the incubation container 14 based on the container shape specified from the type of the incubation container 14, and the concentration of the culture (S205). Incidentally, the concentration of the culture in this S206 is determined by the image processing section 55 based on measurement results at the plural measurement points.

Step 207: The image processing section 55 determines whether the estimated value of the culture amount inside the incubation container 14 (S206) is within a predetermined range or not. When the estimated value is within the predetermined range (YES side), the process goes to S208. On the other hand, when the estimated value deviates from the predetermined range (NO side), the process goes to S209.

Step 208: In this case, the image processing section 55 outputs a normal signal showing that "the culture amount is appropriate" to the CPU 61.

Step 209: In this case, the image processing section 55 outputs an error signal showing that "the culture amount is little" or "the culture amount is much" to the CPU 61.

(Detection of Scattering of Culture)

Figure 13:
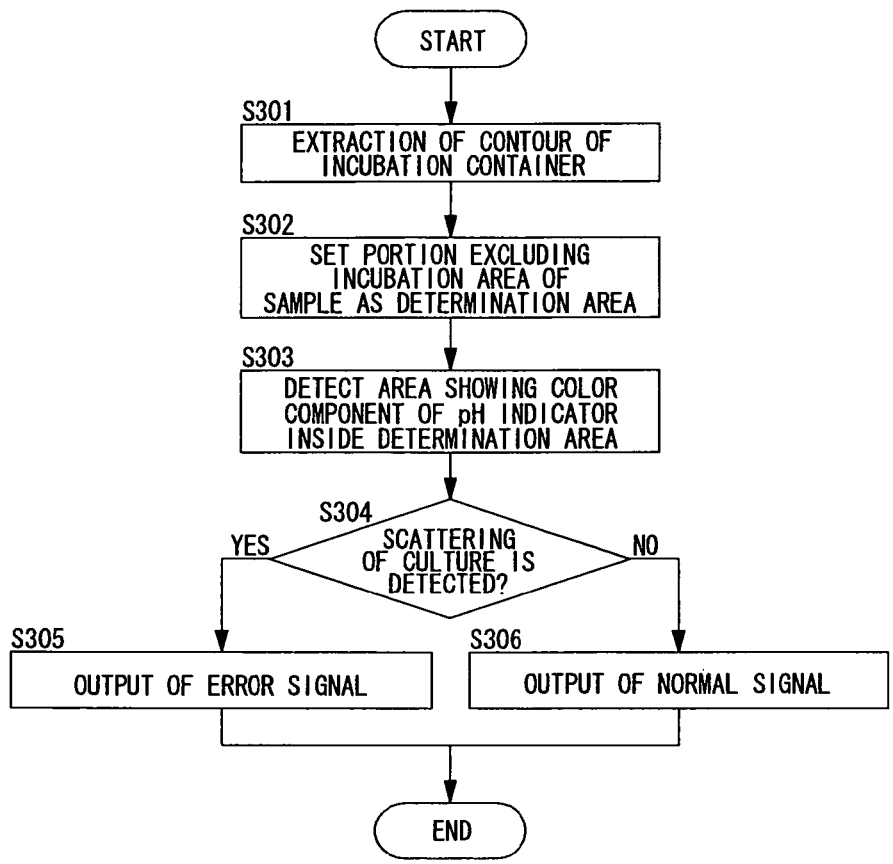
FIG. 13 is a flowchart showing operations in "Detection of Scattering of Culture".

Next, the "detection of the scattering of the culture" in the above-stated S105 is described in detail following a flowchart in FIG. 13. A possibility in which a contamination to the other incubation containers may occur is high when there is the scattering of the culture. Accordingly, it is necessary to detect the scattering of the culture in early time. Incidentally, S301 in FIG. 13 corresponds to the above-stated S201, and therefore, a redundant description is not given.

Figure 14:
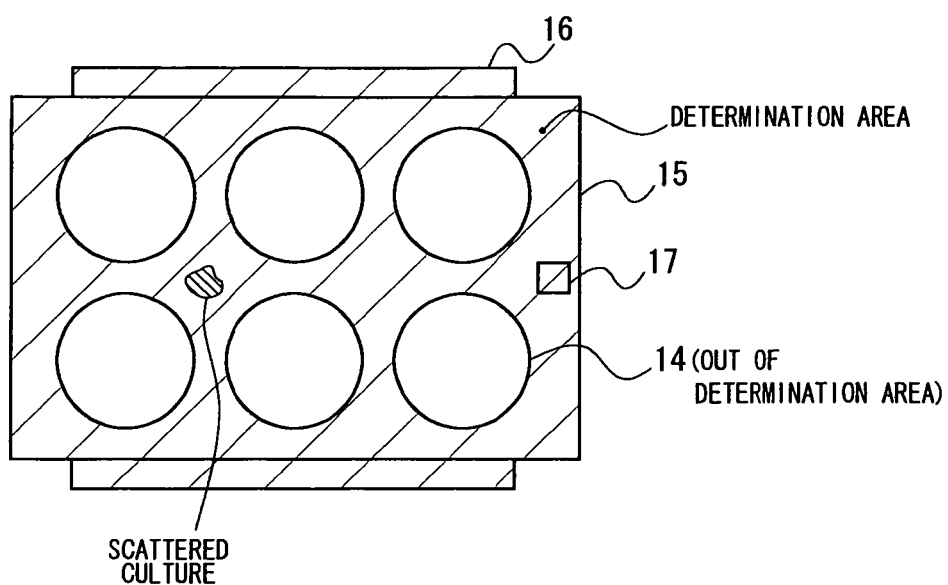
FIG. 14 is an explanatory view showing a determination area in the "Detection of Scattering of Culture".

Step 302: The image processing section 55 performs the pattern matching between the contour data of the incubation container 14 (S301) and the contour template of the incubation container 14, and specifies the area in which the inside of the incubation container is photographed (the incubation area of the sample). Incidentally, when one incubation container 14 has the plural individual small containers, the above-stated incubation area is specified by each small container. The image processing section 55 sets a portion excluding the incubation area of the sample inside of the incubation container 14 as a determination area (refer to FIG. 14).

Step 303: The image processing section 55 detects an area showing the color component of the pH indicator in the determination area. Incidentally, when there is the area having the above-stated color component within the determination area, it can be judged that there is the scattering of the culture.

Step 304: The image processing section 55 determines whether the scattering of the culture is detected from the determination area or not. When it is detected (YES side), the process goes to S305. On the other hand, when it is not detected (NO side), the process goes to S306.

Step 305: In this case, the image processing section 55 outputs an error signal showing that "there is the scattering of the culture" to the CPU 61.

Step 306: On the other hand, in this case, the image processing section 55 outputs a normal signal showing that "the scattering of the culture is not recognized" to the CPU 61.

(Detection of Mold Inside Incubation Container)

Figure 15:
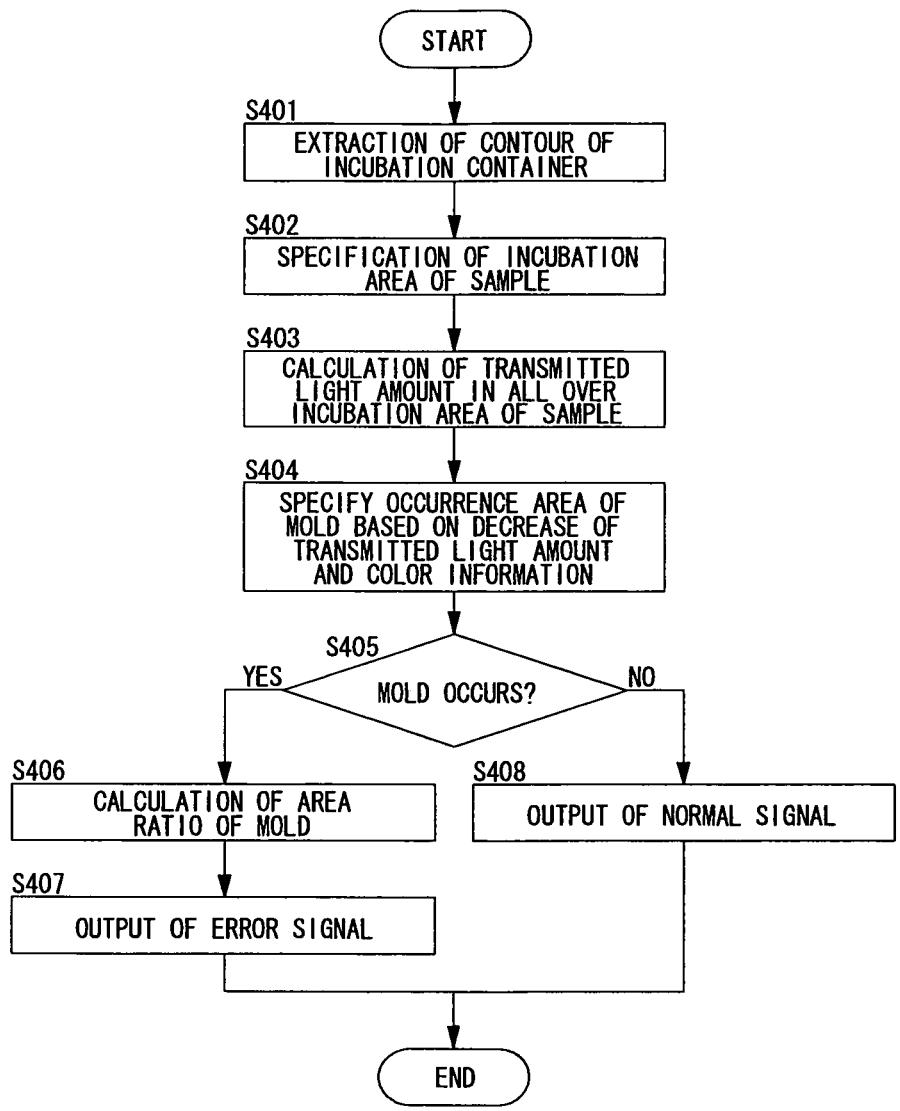
FIG. 15 is a flowchart showing operations in "Detection of Mold inside Incubation Container".

Next, the "detection of the mold inside the incubation container" in the above-stated S105 is described in detail following a flowchart in FIG. 15. When the mold is occurred inside an incubation container, a possibility in which the mold increases also in the other incubation containers is high. Accordingly, it is necessary to detect the occurrence of the mold in early time.

Here, when the detection of the mold inside the incubation container 14 is performed, it is necessary to photograph the total observing image by illuminating the incubation container 14 with the second illumination section 52 from an opposite side of the container observation system 54 in S104. Incidentally, S401 and S402 in FIG. 15 are respectively corresponding to the above-stated S201 and S202, and therefore, redundant descriptions are not given.

Step 403: The image processing section 55 calculates a transmitted light amount in all over the incubation area of the sample (S402). This data of the transmitted light amount in S403 becomes a reference when the image processing section 55 determines a decrease of the transmitted light amount caused by the mold.

Step 404: The image processing section 55 scans the incubation area of the sample (S402) in a constant direction, to detect an area where the transmitted light amount decreases more than a threshold value. The image processing section 55 confirms color information of the detected area, and specifies the occurrence area of the mold. When the mold occurs, the transmitted light amount of the culture decreases significantly, and a color change such that the culture becomes white can be recognized if the mold is, for example, mildew. Accordingly, the image processing section 55 can detect the occurrence of the mold by the above-stated operations.

Step 405: The image processing section 55 determines whether the mold is detected inside the incubation container 14 or not. When the mold is detected (YES side), the process goes to S406. On the other hand, when the mold is not detected (NO side), the process goes to S408.

Step 406: The image processing section 55 calculates an area ratio of the mold relative to the incubation container 14 from a size of the occurrence area of the mold (S404) and the shape of the incubation container 14. Incidentally, there is a case when this process in S406 is omitted by the image processing section in accordance with a setting at the operation instruction section 62.

Step 407: The image processing section 55 outputs an error signal showing that "the mold is occurred inside the incubation container" to the CPU 61. At this time, the data of the area ratio of the mold in S406 may be simultaneously output to the CPU 61.

Step 408: On the other hand, in this case, the image processing section 55 outputs a normal signal showing that "the occurrence of the mold is not recognized inside the incubation container" to the CPU 61.

(Detection of Positional Displacement of Incubation Container)

Figure 16:
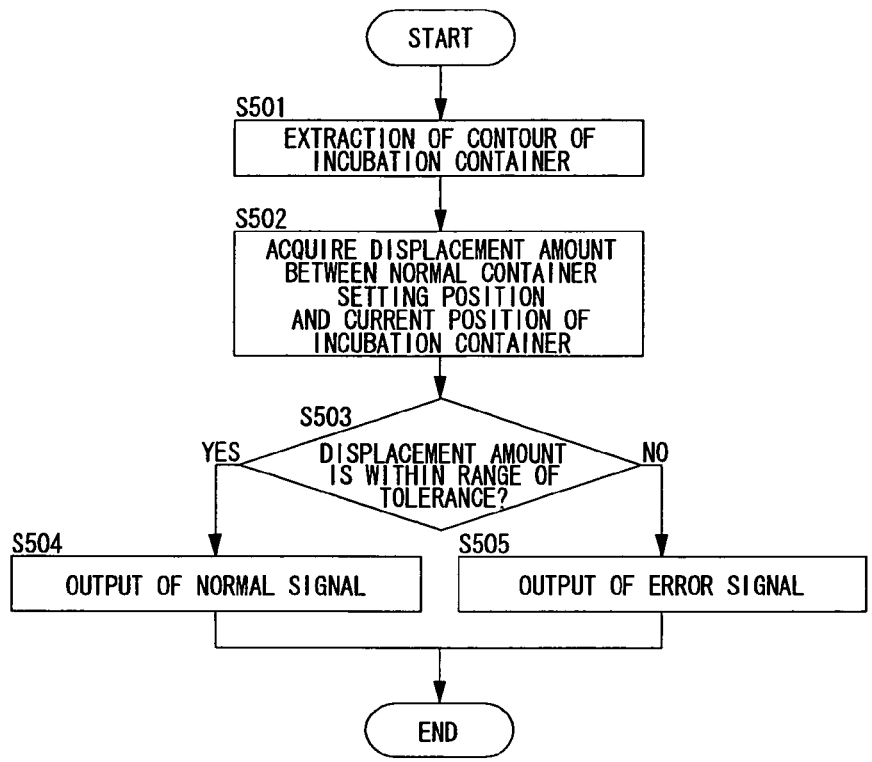
FIG. 16 is a flowchart showing operations in "Detection of Positional Displacement of Incubation Container".

Next, the "detection of the positional displacement of the incubation container" in the above-stated S105 is described in detail following a flowchart in FIG. 16. A possibility becomes high, in which an accident may occur at a carrying time of the incubation container under a state in which the container carrying mechanism does not operate normally. Accordingly, it becomes necessary to confirm the operation state of the container carrying mechanism by a presence/absence of the positional displacement of the incubation container. Incidentally, S501 in FIG. 16 corresponds to the above-stated S201, and therefore, a redundant description is not given.

Figure 17:
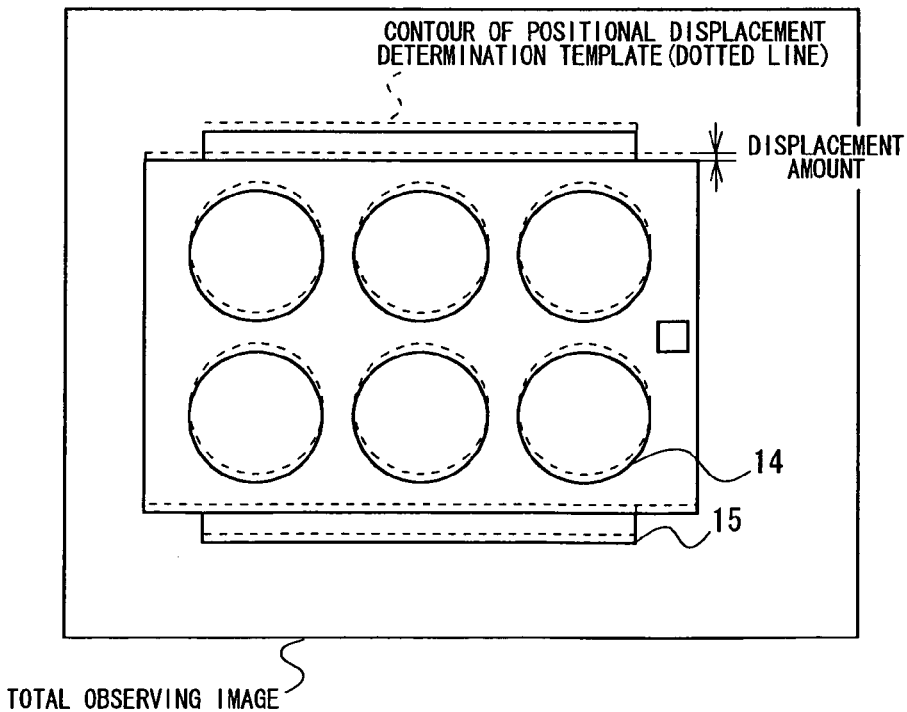
FIG. 17 is an explanatory view of the "Detection of Positional Displacement of Incubation Container".

Step 502: The image processing section 55 reads data of a positional displacement determination template from the database section 63. This positional displacement determination template corresponds to the contours of the incubation containers 14 at normal container setting positions. Consequently, the contours of the incubation containers 14 extracted from the total observing image and the contours of the positional displacement determination template are matched under a state in which the container carrying mechanism 37 operates normally. The image processing section 55 performs a matching between the contour data of the incubation container 14 (S501) and the positional displacement determination template, and acquires a displacement amount between the normal container setting positions and the current positions of the incubation containers (refer to FIG. 17).

Step 503: The image processing section 55 determines whether the above-stated displacement amount (S502) falls within a range of a tolerance or not. When the displacement amount falls within the range of the tolerance (YES side), the process goes to S504. On the other hand, when the displacement amount does not fall within the range of the tolerance (NO side), the process goes to S505.

Step 504: In this case, the image processing section 55 outputs a normal signal showing that "the container carrying mechanism operates normally" to the CPU 61.

Step 505: On the other hand, in this case, the image processing section 55 outputs an error signal showing that "the operation of the container carrying mechanism is abnormal" to the CPU 61.

(Detection of Dew Condensation Inside Incubation Container)

Figure 18:
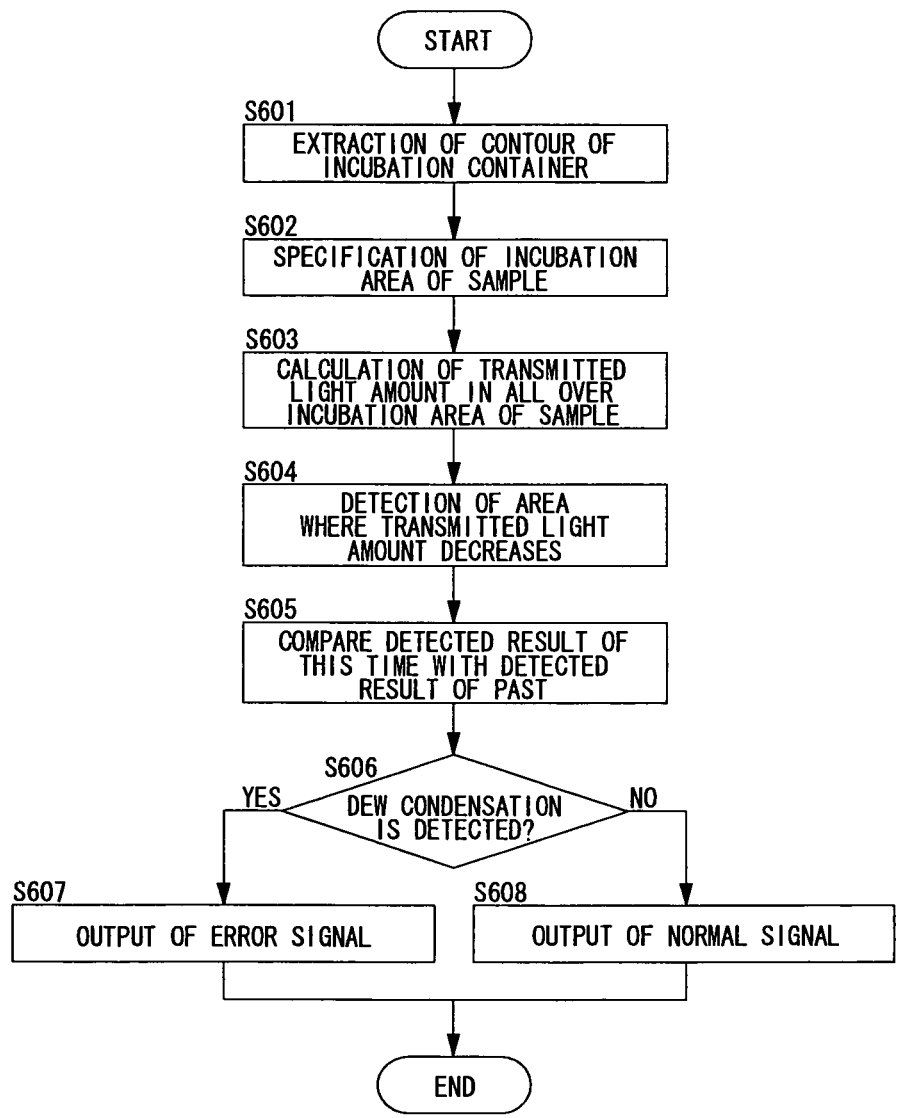
FIG. 18 is a flowchart showing operations in "Detection of Dew Condensation inside Incubation Container".

Next, the "detection of the dew condensation inside the incubation container" in the above-stated S105 is described in detail following a flowchart in FIG. 18. The dew condensation occurs inside the incubation container when there is temperature unevenness resulting from a trouble of a temperature adjustor and so on, and an operation of a motor and so on. If the dew condensation is detected, it becomes possible to confirm the incubation state of the sample, and to improve an incubation accuracy further more.

Here, when the detection of the dew condensation inside the incubation container is performed, it is necessary to photograph the total observing image by illuminating the incubation container 14 with the second illumination section 52 from the opposite side of the container observation system 54 in S104. Besides, in the detection of the dew condensation inside the incubation container 14, an analysis is performed by using plural total observing images photographed at different times. Incidentally, S601 and S602 in FIG. 18 respectively correspond to the above-stated S201 and S202, and therefore, redundant descriptions are not given.

Step 603: The image processing section 55 calculates the transmitted light amount in all over the incubation area of the sample (S602). Data of the transmitted light amount in this S603 becomes a reference when the image processing section 55 determines a decrease of the transmitted light amount caused by the dew condensation. Besides, the image processing section 55 acquires a luminance level of a measurement reference point (not-shown) existing at a predetermined position of the holder in the total observing image.

Step 604: The image processing section 55 scans the incubation area of the sample (S602) in the constant direction, and detects an area where the transmitted light amount decreases more than a threshold value. Besides, the image processing section 55 records a detected result of this time and the luminance level of the measurement reference point to the database section 63 after the detection process in S604.

Step 605: The image processing section 55 reads the detected result of a previous time from the database section 63, and performs a comparison with the detected result of this time (S604). At this time, the image processing section 55 performs the comparison after normalizing the value of the transmitted light amounts between the plural images based on the luminance level of the measurement reference point.

Step 606: The image processing section 55 determines whether the dew condensation occurs inside the incubation container 14 or not. Concretely speaking, the image processing section 55 determines that the dew condensation occurs when the decrease of the transmitted light amount becomes larger than the previous time. It goes without saying that the image processing section 55 may perform the determination by using the determination result before the previous time. Incidentally, a damping of the transmitted light amount in case of the dew condensation is smaller than the case of the mold, and the color change such as the mold does not occur, and therefore, it is fully possible to distinguish between both.

When the dew condensation occurs (YES side), the process goes to S607. On the other hand, when the dew condensation does not occur (NO side), the process goes to S608.

Step 607: In this case, the image processing section 55 outputs an error signal showing that "the dew condensation occurs" to the CPU 61. At this time, the image processing section 55 may estimate a droplet amount inside the incubation container by the change of the luminance value, the estimation of the culture amount, and so on in the total observing image.

Step 608: On the other hand, in this case, the image processing section 55 outputs a normal signal showing that "the dew condensation does not occur" to the CPU 61.

(Effect of Present Embodiment)

The incubator 11 of the present embodiment automatically detects the change of the culture amount, the occurrence of the mold, the scattering of the culture, and so on, and performs the carrying out of the incubation container 14 and the predetermined warning operations when something is wrong with the environment state surrounding the incubation container 14. Accordingly, a manual labor of the confirmation of the incubation state of the sample is reduced significantly, and it becomes easy to keep the incubation state of the sample in the temperature-controlled room 21 in good state.

Besides, it is possible for the incubator 11 of the present embodiment to automatically detect the positional displacement of the incubation container 14 resulting from the abnormality of the container carrying mechanism 37 and the dew condensation of the incubation container 14 caused by the temperature unevenness of the temperature-controlled room 21, and to perform the predetermined warning operations. Accordingly, it is possible to drastically suppress the occurrence of accidents resulting from the abnormality of the incubation apparatus.

Further, the incubator 11 of the present embodiment photographs the microscopic observed image of the sample in accordance with the predetermined schedule, and records the image data as a database. Accordingly, it becomes possible to significantly reduce the manual labor of the confirmation of the incubation condition of the sample, and to judge timings and so on of the culture exchange or the subculture by the user based on the image data.

(Supplemental Matters of Embodiment)

(1) Respective configurations of the incubator of the present invention are not limited to the above-stated embodiment. For example, the present invention can be applied to a multi-gas incubator capable of adjusting at least one of oxygen concentration or nitrogen concentration in addition to the carbon dioxide concentration. Besides, the adjustment of the humidity may be performed by a humidification water reservoir storing humidification water and a temperature adjustor controlling a water temperature of the humidification water reservoir (both are not shown).

(2) A macro observation system capable of microscopic observation with lower magnification than the microscopic observation system may be provided as the observation unit of the above-stated embodiment. When the microscopic observation is performed, two kinds of sample observing images by the macro observation system and the microscopic observation system may be photographed in a series of sequence. Besides, in the above-stated embodiment, the image analysis may be performed not by the observation unit but by the CPU.

(3) The incubator of the present invention may have a configuration selectively performing either of the estimation of the culture amount, the detection of the scattering of the culture, the detection of the mold, the detection of the positional displacement of the incubation container, and the detection of the dew condensation.

Besides, in the detection of the positional displacement of the incubation container and the detection of the scattering of the culture, it is possible to determine by using the extracted contours, and therefore, the total observing image may be a gray scale image when only these determination are performed. Incidentally, in the detection of the positional displacement of the incubation container, markers may be disposed at plural points of the incubation container to detect the abnormality of the container carrying mechanism from positional displacements of the markers.

(4) In S108 of the above-stated embodiment, the discharge of the incubation container and the warning operation (S109) may be performed simultaneously. Besides, in S109 of the above-stated embodiment, the incubation container may be temporary returned to the stacker after the warning operation.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to exact construction and operation illustrated and described, and accordingly all suitable modifications and equivalents may be resorted to, falling within the scope thereof.

The invention claimed is:

1. An incubation apparatus including a temperature-controlled room adjusted to be a predetermined environment condition suitable for incubating cells, and incubating a sample of an incubation container inside the temperature-controlled room, the incubation apparatus comprising:
   an imaging section that photographs an entirety of the incubation container and an area external of the incubation container inside the temperature-controlled room to generate a total observing image that includes image information concerning a contour of the incubation container;
   an image analyzing section that is capable of determining (i) an occurrence of a scattering of a culture by analyzing the image information concerning the contour of the incubation container, and (ii) whether it is necessary to issue an error signal notifying the occurrence of the scattering of the culture in accordance with the analysis result;
   a microscope unit that is capable of photographing a sample observing image in which a sample inside the incubation container is microscopically observed, and
   a controller that controls the image analyzing section and the microscope unit,
   wherein after the total observing image is generated by the imaging section, the controller:
   instructs the image analyzing section to determine (i) the occurrence of the scattering of the culture by analyzing the image information concerning the contour of the incubation container, and (ii) whether it is necessary to issue the error signal notifying the occurrence of the scattering of the culture,
   instructs the image analyzing section to issue the error signal when it is determined that it is necessary to issue the error signal, and
   instructs the microscope unit to photograph the sample observing image in which the sample inside the incubation container is microscopically observed at predetermined time intervals, when it is determined that it is not necessary to issue the error signal.

2. The incubation apparatus according to claim 1, further comprising
   a carrying apparatus that is capable of carrying the incubation container in the temperature-controlled room.

3. The incubation apparatus according to claim 2, wherein the controller instructs the carrying apparatus to carry the incubation container out of the temperature-controlled room when the error signal is output.

4. The incubation apparatus according to claim 1, wherein the controller instructs a notifying device to perform a warning operation to outside of the incubation apparatus when the error signal is output.

5. The incubation apparatus according to claim 1, wherein when the error signal is output, the controller determines whether it is necessary to move the incubation container out of the temperature-controlled room based on a predetermined condition.

6. The incubation apparatus according to claim 5, wherein when it is determined that it is necessary to move the incubation container out of the temperature-controlled room, the controller instructs a carrying apparatus to move the incubation container out of the temperature-controlled room, and
   when it is determined that it is not necessary to move the incubation container out of the temperature-controlled room, the controller issues a warning notifying an occurrence of abnormality.

7. The incubation apparatus according to claim 1, wherein both the imaging section and the microscope unit are disposed over the incubation container, and photograph from over the incubation container.

8. The incubation apparatus according to claim 1, wherein the image analyzing section is also capable of determining an occurrence of a positional displacement of the incubation container, and
   the controller instructs the image analyzing section to determines the occurrence of the positional displacement of the incubation container.

9. The incubation apparatus according to claim 8, wherein the image analyzing section determines the occurrence of the positional displacement of the incubation container by comparing the contour of the incubation container and a contour of a positional displacement determination template.

10. An incubation apparatus including a temperature-controlled room adjusted to be a predetermined environment condition suitable for incubating cells, and incubating a sample of an incubation container inside the temperature-controlled room, the incubation apparatus comprising:
    an imaging section that photographs an entirety of the incubation container and an area external of the incubation container inside the temperature-controlled room to generate a total observing image that includes image information concerning an inside of the incubation container;
    an image analyzing section that is capable of (i) determining an occurrence of a scattering of a culture by analyzing the image information concerning the inside of the incubation container, (ii) determining whether it is necessary to issue an error signal notifying the occurrence of the scattering of the culture in accordance with the analysis result, (iii) detecting dew condensation inside the incubation container based on a change of a transmitted light amount inside the incubation container, and (iv) outputting another error signal when the dew condensation is detected;
    a microscope unit that is capable of photographing a sample observing image in which a sample inside the incubation container is microscopically observed, and
    a controller that controls the image analyzing section and the microscope unit,
    wherein after the total observing image is generated by the imaging section, the controller:
    instructs the image analyzing section to determine (i) the occurrence of the scattering of the culture by analyzing the image information concerning the contour of the incubation container, and (ii) whether it is necessary to issue the error signal notifying the occurrence of the scattering of the culture, instructs the image analyzing section to issue the error signal when it is determined that it is necessary to issue the error signal, instructs the microscope unit to photograph the sample observing image in which the sample inside the incubation container is microscopically observed at predetermined time intervals, when it is determined that it is not necessary to issue the error signal, and instructs the image analyzing section to detect the dew condensation inside the incubation container, and output the other error signal when the dew condensation is detected.

11. The incubation apparatus according to claim 10, further comprising
a carrying apparatus that carries the incubation container in the temperature-controlled room.

12. The incubation apparatus according to claim 11, wherein
the carrying apparatus carries the incubation container out of the temperature-controlled room when the error signal is output.

13. The incubation apparatus according to claim 10, further comprising
a notifying device that performs a warning operation to outside of the incubation apparatus when the error signal is output.

14. An incubation apparatus including a temperature-controlled room adjusted to be a predetermined environment condition suitable for incubating cells, and incubating a sample of an incubation container inside the temperature-controlled room, the incubation apparatus comprising:

an imaging section that photographs an entirety of the incubation container and an area external of the incubation container inside the temperature-controlled room to generate a total observing image that includes image information concerning a contour and an inside of the incubation container;

an image analyzing section that is capable of (i) determining an occurrence of a scattering of a culture by analyzing the image information concerning the contour of the incubation container, (ii) determining whether it is necessary to issue an error signal notifying the occurrence of the scattering of the culture in accordance with an analysis result, (iii) estimating a culture amount inside the incubation container based on luminance and a ratio of respective color components inside the incubation container, and (iv) outputting another error signal when an estimated value of the culture amount deviates from a setting range;

a microscope unit that is capable of photographing a sample observing image in which a sample inside the incubation container is microscopically observed, and a controller that controls the image analyzing section and the microscope unit, wherein after the total observing image is generated by the imaging section, the controller:

instructs the image analyzing section to determine (i) the occurrence of the scattering of the culture by analyzing the image information concerning the contour of the incubation container, and (ii) whether it is necessary to issue the error signal notifying the occurrence of the scattering of the culture, instructs the image analyzing section to issue the error signal when it is determined that it is necessary to issue the error signal, instructs the microscope unit to photograph the sample observing image in which the sample inside the incubation container is microscopically observed at predetermined time intervals, when it is determined that it is not necessary to issue the error signal, and instructs the image analyzing section to estimate the culture amount inside the incubation container, and output the other error signal when the estimated value of the culture amount deviates from the setting range.

15. The incubation apparatus according to claim 14, further comprising
a carrying apparatus that carries the incubation container in the temperature-controlled room.

16. The incubation apparatus according to claim 15, wherein
the carrying apparatus carries the incubation container out of the temperature-controlled room when the error signal is output.

17. The incubation apparatus according to claim 14, further comprising
a notifying device that performs a warning operation to outside of the incubation apparatus when the error signal is output.

18. An incubation apparatus including a temperature-controlled room adjusted to be a predetermined environment condition suitable for incubating cells, and incubating a sample of an incubation container inside the temperature-controlled room, the incubation apparatus comprising:

an imaging section that photographs an entirety of the incubation container and an area external of the incubation container inside the temperature-controlled room to generate a total observing image that includes image information concerning a contour and an inside of the incubation container;

an image analyzing section that is capable of (i) determining an occurrence of a scattering of a culture by analyzing the image information concerning the contour of the incubation container, (ii) determining whether it is necessary to issue an error signal notifying the occurrence of the scattering of the culture in accordance with the analysis result, (iii) detecting an occurrence of mold inside the incubation container based on a transmitted light amount and color information inside the incubation container, and (iv) outputting another error signal when the mold occurs;

a microscope unit that is capable of photographing a sample observing image in which a sample inside the incubation container is microscopically observed, and a controller that controls the image analyzing section and the microscope unit, wherein after the total observing image is generated by the imaging section, the controller:

instructs the image analyzing section to determine (i) the occurrence of the scattering of the culture by analyzing the image information concerning the contour of the incubation container, and (ii) whether it is necessary to issue the error signal notifying the occurrence of the scattering of the culture, instructs the image analyzing section to issue the error signal when it is determined that it is necessary to issue the error signal, instructs the microscope unit to photograph the sample observing image in which the sample inside the incubation container is microscopically observed at predetermined time intervals, when it is determined that it is not necessary to issue the error signal, and instructs the image analyzing section to detect the occurrence of mold inside the incubation container, and output the other error signal when the mold occurs.

19. The incubation apparatus according to claim 18, further comprising;
   a carrying apparatus that carries the incubation container in the temperature-controlled room.

20. The incubation apparatus according to claim 19, wherein
   the carrying apparatus carries the incubation container out of the temperature-controlled room when the error signal is output.

21. The incubation apparatus according to claim 18, further comprising
   a notifying device that performs a warning operation to outside of the incubation apparatus when the error signal is output.

22. An incubation apparatus including a temperature-controlled room adjusted to be a predetermined environment condition suitable for incubating cells, and incubating a sample of an incubation container inside the temperature-controlled room, the incubation apparatus comprising:
   an imaging section that photographs an entirety of the incubation container and an area external of the incubation container inside the temperature-controlled room to generate a total observing image that includes image information concerning a contour of the incubation container;
   an image analyzing section that is capable of determining (i) an occurrence of a scattering of a culture by analyzing the image information concerning the contour of the incubation container, and (ii) whether it is necessary to issue an error signal notifying the occurrence of the scattering of the culture in accordance with the analysis result;
   a microscope unit that is capable of photographing a sample observing image in which a sample inside the incubation container is microscopically observed, and
   a controller that controls the image analyzing section and the microscope unit,
   wherein after the total observing image is generated by the imaging section, the controller:
   instructs the image analyzing section to determine (i) the occurrence of the scattering of the culture by analyzing the image information concerning the contour of the incubation container, and (ii) whether it is necessary to issue the error signal notifying the occurrence of the scattering of the culture,
   instructs the image analyzing section to issue the error signal when it is determined that it is necessary to issue the error signal,
   instructs the microscope unit to photograph the sample observing image in which the sample inside the incubation container is microscopically observed at predetermined time intervals, when it is determined that it is not necessary to issue the error signal, and
   the image analyzing section determines the occurrence of the scattering of the culture by analyzing image information of a determination area which is an area excluded an incubation area from the contour of the incubation container.

* * * * *